US010799262B2

(12) United States Patent
Chae

(10) Patent No.: US 10,799,262 B2
(45) Date of Patent: Oct. 13, 2020

(54) SNARE FOR REMOVING TUMOR

(71) Applicant: The Catholic University of Korea Industry-Academic Cooperation Foundation, Seoul (KR)

(72) Inventor: Hiun-suk Chae, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 109 days.

(21) Appl. No.: 16/069,459

(22) PCT Filed: Apr. 5, 2016

(86) PCT No.: PCT/KR2016/003502
§ 371 (c)(1),
(2) Date: Jul. 11, 2018

(87) PCT Pub. No.: WO2017/122874
PCT Pub. Date: Jul. 20, 2017

(65) Prior Publication Data
US 2019/0015130 A1    Jan. 17, 2019

(30) Foreign Application Priority Data
Jan. 14, 2016  (KR) ........................ 10-2016-0004662

(51) Int. Cl.
*A61B 17/3205*    (2006.01)
*A61B 17/221*    (2006.01)
(Continued)

(52) U.S. Cl.
CPC .. *A61B 17/32056* (2013.01); *A61B 17/12013* (2013.01); *A61B 17/221* (2013.01);
(Continued)

(58) Field of Classification Search
CPC ........ A61B 2017/00358; A61B 17/221; A61B 2017/2212; A61B 2017/2215;
(Continued)

(56) References Cited

U.S. PATENT DOCUMENTS

| 5,741,271 A | * | 4/1998 | Nakao ..................... A61B 1/015 604/523 |
| 5,814,052 A | | 9/1998 | Nakao et al. |

(Continued)

FOREIGN PATENT DOCUMENTS

| KR | 10-0937177 | 7/2005 |
| KR | 10-2012-0042136 | 3/2012 |
| WO | 2015/003982 A2 | 1/2015 |

OTHER PUBLICATIONS

Merriam-Webster definition for "spread" as accessed Feb. 20, 2020; https://www.merriam-webster.com/dictionary/spread.*

*Primary Examiner* — Wade Miles
(74) *Attorney, Agent, or Firm* — Hoffmann & Baron, LLP

(57) ABSTRACT

Disclosed herein is a snare (transparent cap) for removing a polyp which includes a stalk and a head connected to the stalk, wherein the snare includes: a body having a hollow tubular shape and an interior of which is partitioned into a plurality of chambers; a ring mounted to at least part of the body using elasticity; a first snare discharged outside the body through a first chamber among the plurality of chambers and hooks the stalk; and a second snare which is discharged outside the body through a second chamber among the plurality of chambers, wherein when the stalk is spread according to pulling the first snare that hooks the stalk, and the second snare pulls a first portion in a lower end of the stalk as spread including the head, the ring is discharged from the body and shrinks through the elasticity and then fixes the first portion.

1 Claim, 17 Drawing Sheets

(51) Int. Cl.
*A61B 17/12* (2006.01)
*A61B 18/14* (2006.01)
*A61B 17/00* (2006.01)
*A61B 18/00* (2006.01)

(52) U.S. Cl.
CPC ............ *A61B 18/14* (2013.01); *A61B 18/148* (2013.01); *A61B 2017/0034* (2013.01); *A61B 2017/00349* (2013.01); *A61B 2017/00353* (2013.01); *A61B 2017/00358* (2013.01); *A61B 2017/00818* (2013.01); *A61B 2017/12004* (2013.01); *A61B 2017/12018* (2013.01); *A61B 2017/2215* (2013.01); *A61B 2018/00178* (2013.01); *A61B 2018/00196* (2013.01); *A61B 2018/00577* (2013.01); *A61B 2018/00589* (2013.01); *A61B 2018/141* (2013.01)

(58) Field of Classification Search
CPC ........ A61B 2017/2217; A61B 2017/17; A61B 2017/22031; A61B 2017/22035; A61B 17/22032; A61B 17/32056; A61B 17/12; A61B 17/120069; A61B 17/12013; A61B 2017/12018; A61B 10/02; A61M 25/0071; A61M 25/0026; A61M 25/0032; A61M 2025/0036; A61M 2025/0037; A61M 2025/0039; A61M 2025/004
See application file for complete search history.

(56) References Cited

U.S. PATENT DOCUMENTS

| | | | | |
|---|---|---|---|---|
| 6,315,782 | B1* | 11/2001 | Chu | A61B 17/12013 606/113 |
| 6,517,539 | B1* | 2/2003 | Smith | A61B 17/32056 606/113 |
| 2003/0065246 | A1 | 4/2003 | Inman et al. | |
| 2004/0059345 | A1 | 3/2004 | Nakao et al. | |
| 2006/0253128 | A1 | 11/2006 | Sekine et al. | |
| 2008/0287965 | A1* | 11/2008 | Ducharme | A61B 17/12013 606/140 |
| 2008/0312496 | A1* | 12/2008 | Zwolinski | A61B 17/00234 600/104 |
| 2009/0105728 | A1* | 4/2009 | Noda | A61B 17/12013 606/139 |
| 2009/0198255 | A1* | 8/2009 | Ikeda | A61B 17/0401 606/140 |
| 2011/0087281 | A1* | 4/2011 | Fischvogt | A61B 17/0401 606/232 |
| 2012/0239061 | A1* | 9/2012 | Mathur | A61F 5/0083 606/140 |
| 2014/0171733 | A1* | 6/2014 | Sternik | A61B 17/12122 600/37 |
| 2014/0249550 | A1* | 9/2014 | Mullins | A61B 17/12013 606/140 |

\* cited by examiner

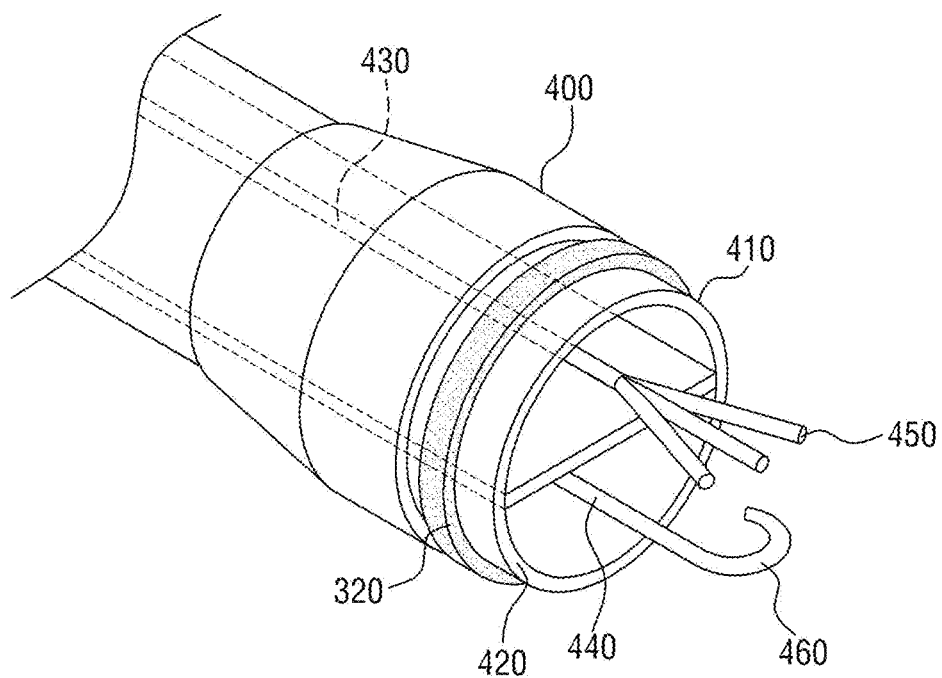
FIG. 6C
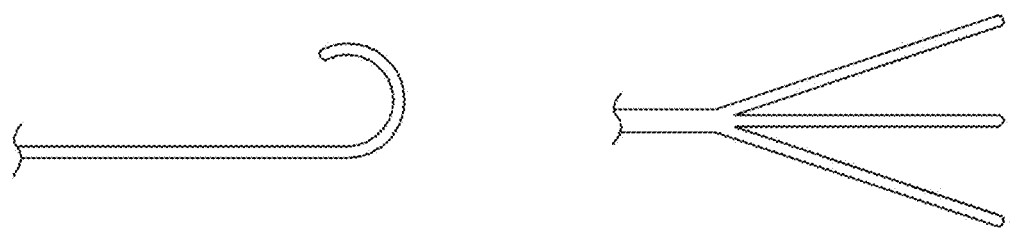
FIG. 6A
FIG. 6B

SNARE FOR REMOVING TUMOR

CROSS-REFERENCE TO RELATED APPLICATIONS

The present application is the U.S. National Phase of PCT/KR2016/003502, filed on Apr. 5, 2016, which claims priority to Korean Patent Application No. 10-2016-0004662, filed on Jan. 14, 2016, the entire contents of which are incorporated herein by reference.

BACKGROUND

Technical Field

The present invention relates to a snare (transparent cap) for removing a tumor. Specifically, the present invention relates to a medical two-chamber snare (transparent cap) used when performing polypectomy, wherein a snare made of a special metal is introduced through a working channel of an endoscope, and then electricity is passed through when grasping a polyp so as to cut it.

Description of the Related Art

In general, colonoscopic polypectomy cuts polyps by introducing a punch forceps or a snare made of a special metal through a working channel of an endoscope.

When performing this colonoscopic polypectomy, small polyps are cut with a punch forceps. Meanwhile, big polyps are removed by either passing electricity through when the polyp is grasped with a snare, or physically cutting the polyp.

In addition, if polyps are large and broadly attached to the colon mucosa, submucosal injection of saline is involved so as to reduce electrical damage to the colon wall before excising the polyps with a snare (EMR, ESD endoscopic mucosal resection, endoscopic submucosal dissection).

Commonly, a snare used for polypectomy is formed with a tensile rope, wherein the tensile rope ends at the front end portion by being inserted into the snare having a semicircle like shape and the snare has a peak.

The tensile rope is guided to move easily inside a bushing and a corresponding stopper member, wherein the corresponding stopper member has a pipe shape and is disposed at an end portion of the bushing. As one end portion of two snare legs is fixed to the tensile rope, the snare is consequently transferred from a storage position where the snare is placed inside the bushing in a state of being elongated by the tensile rope, to a use position where the snare is placed in the front of an end portion of the bushing.

In addition, an end portion of another snare leg being inside the bushing is connected to a stopper which moves toward the corresponding stopper when taking out the snare from the bushing. Consequently, if the snare leg continues its moving, the snare is expanded into a semicircle shape.

For another example, a radiofrequency ablation device capable of supplying a current may be applied to the aforementioned type of snare.

In this case, the snare acts as an electrode and is used so as to excise one or a plurality of polyps, such as adenoids, being inside the abdominal cavity, especially intestines, by using a radiofrequency current.

Therefore, when performing polypectomy, an endoscopist commonly grasps a polyp with the snare inserted into the abdominal cavity by using the endoscope, then followed by excision.

When removing a pedunculated polyp (Ip polyp) with a stalk, in the case of a polyp with a stalk having a thickness of 5 mm and less, such a polyp is removed by applying an electric current, which is then followed by coagulation. However, should a polyp with a stalk having a thickness of 8 mm and more be excised by merely applying an electric current, since coagulation does not occur sufficiently in a feeding vessel (artery in the stalk), it may result in acute and delayed bleeding.

Further, when the bleeding occurs, since the stalk remaining after excision continues to move, it is difficult to stop the bleeding.

In order to prevent these kinds of complications, Olympus (Japan) has developed "endo-loop". However, it is difficult for a beginner to operate it. Furthermore, it may cause the bleeding when a stalk is thin and thus mechanically cut. Therefore, there is required a method for removing a pedunculated polyp (Ip polyp) regardless of the thickness of a stalk.

Further, since the stalk of a polyp is present in a twisted shape, a conventional snare for polypectomy has a problem in that it is difficult to suck a stalk portion which is adjacent to the head of a polyp, and then to cut it.

Further, since a conventionally used ring is mounted on the outer circumference of the snare, then discharged, time interval occurs when sucking a polyp and fixing it with a ring. There is, thus, a problem in that it is difficult for a user to fix a desired portion of a polyp through the ring.

Therefore, it is required to solve the aforementioned problems.

RELATED ART DOCUMENT

Patent Document (Patent Document 1) Korea Patent Registration No. 10-0937177.

SUMMARY OF THE INVENTION

The present invention is directed to a medical two-chamber snare (transparent cap) used when performing polypectomy, wherein a snare made of a special metal is introduced through a working channel of an endoscope, and then electricity is passed through when grasping a polyp so as to cut it.

Further, various aspects of the present invention are directed to providing a two-chamber snare which spreads a stalk folded loosely through a first chamber, fixes a polyp with a ring through a second chamber, and then clearly removes a head of the polyp, so as to make surgery easier.

Further, differently from the conventional ring, a ring is equipped to only the second chamber in the two-chamber snare. As the polyp is pulled inside the second chamber, then fixed through a fixer, the initial entry direction of the ring may be maintained stably. It is advantageous in an aspect of the structure. Moreover, it may save time and simplify surgery.

Meanwhile, technical problems to be solved in the present invention are not limited to the above-mentioned technical problems, and other technical problems will be clearly understood by those of ordinary skill in the art from the following description.

According to one embodiment of the present invention, provided is a snare (transparent cap) for removing a polyp with a stalk and a head connected to the stalk including: a body which is a hollow tubular shape and of which the interior is partitioned into a plurality of chambers; a ring which is mounted on at least part of the body using elasticity; a first snare which is discharged to the outside through a first chamber among the plurality of chambers and hooks the stalk; and a second snare which is discharged through a second chamber among the plurality of chambers, wherein when the stalk is spread according to pulling of the first snare hooking the stalk, the second snare pulls a first portion in a lower end of the head in the whole portion of the spread stalk, and the ring discharged from the body shrinks through the elasticity and then fixes the pulled first portion.

Further, the ring may be mounted on the outer circumference of the second chamber. When the second snare pulls the first portion into the second chamber, the ring may be instantly discharged to the pulled first portion.

Further, the head may be removed by excising an upper portion of the fixed first portion using a current.

Further, the first snare and the second snare may have at least one of a hook type and a multi-legged type.

The present invention provides a medical two-chamber snare used when performing polypectomy, wherein a snare made of a special metal is introduced through a working channel of an endoscope, and then electricity is passed through when grasping a polyp so as to cut it.

Further, the present invention provides a two-chamber snare which spreads a stalk folded loosely through a first chamber, fixes a polyp with a ring through a second chamber, and then clearly removes a head of the polyp, so as to make surgery easier.

Further, differently from the conventional ring, a ring is equipped to only the second chamber in the two-chamber snare. As the polyp is pulled inside the second chamber, then fixed through a fixer, the initial entry direction of the ring may be maintained stably. It is advantageous in an aspect of the structure. Moreover, it may save time and simplify surgery.

Meanwhile, effects of the present invention are not limited to the aforementioned effects, and other effects not covered will be clearly understood to those of ordinary skilled in the art from the following description.

BRIEF DESCRIPTION OF THE DRAWINGS

FIGS. 2A to 2G show another example of colonoscopic polypectomy according to the present invention.

FIGS. 6A to 6C show a view to explain the structure of a two-chamber snare for removing a tumor according to the present invention.

DETAILED DESCRIPTION OF THE EMBODIMENTS

Hardly does blood flow into the liver because of portal hypertension due to liver cirrhosis. Thus, a large amount of blood makes an easier path toward the direction where a pressure is low, so as to flow through such a path.

That is, if fine blood vessels are expanded from dozens to hundreds of times and more, a part thereof protrudes into the esophagus to form esophageal varices, while another part thereof protrudes into the stomach to form gastric varices.

As an EBL (endoscopic band ligation) at a tip end of the endoscope for preventing and treating Esophageal varix bleeding, a common rubber ring is positioned at a tip end of a transparent cap and the ring is discharged to a bleeding part, so as to strangulate blood vessels and to stop the bleeding.

Figure 1A:
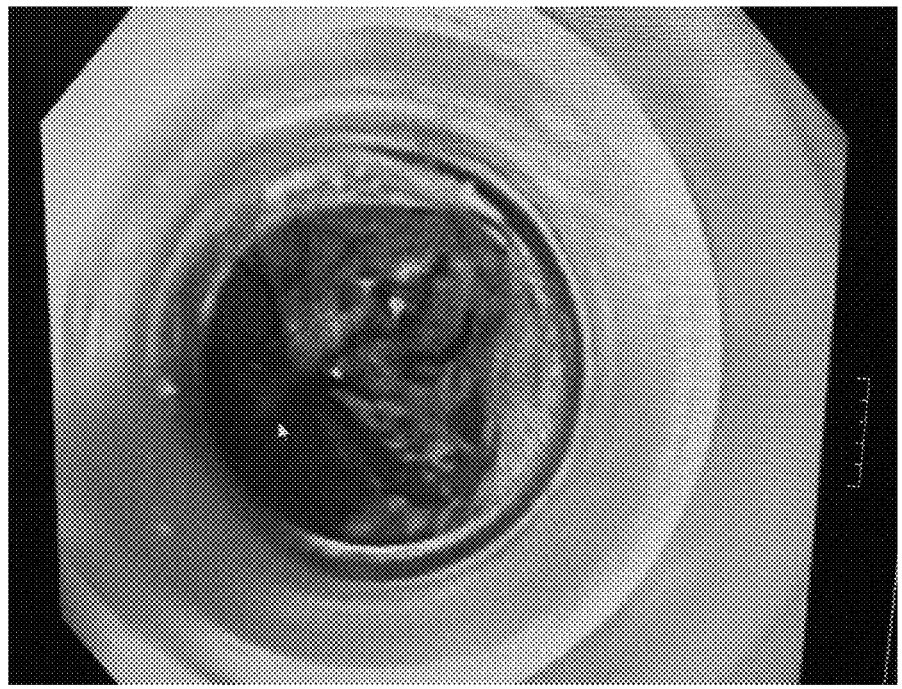
FIGS. 1A and 2B show a specific example of esophageal varix bleeding as a complication of liver cirrhosis according to the present invention.
Figure 1B:
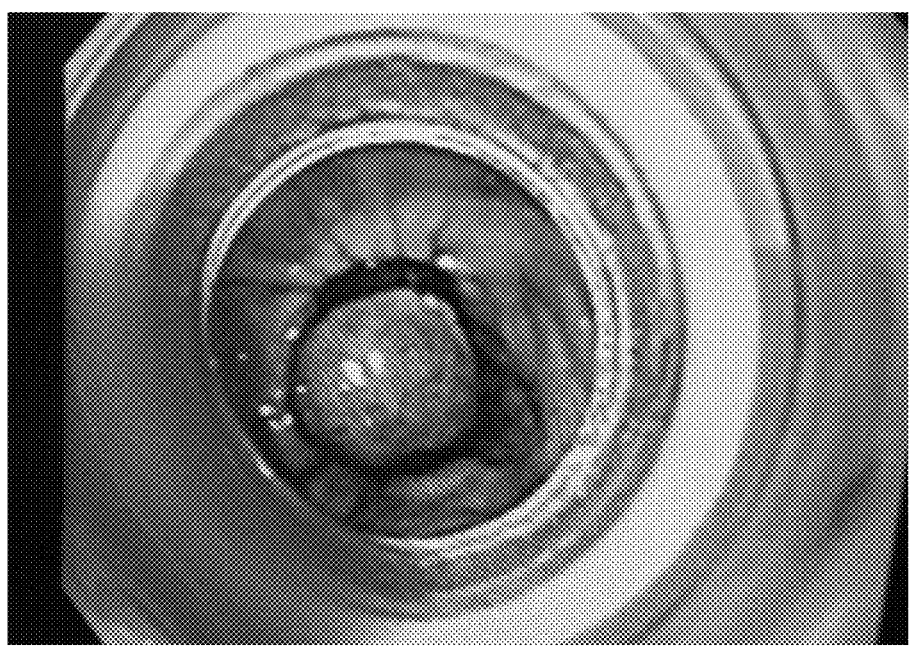
FIG. 1C to FIG. 1K show an example of colonoscopic polypectomy commonly applied according to the present invention.
Figure 1C:
Figure 1D:
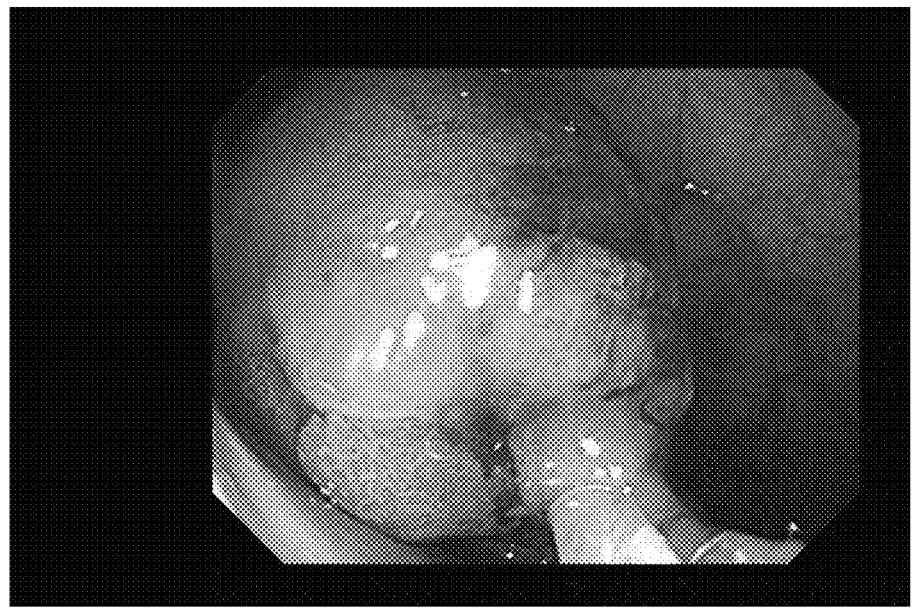
Figure 1E:
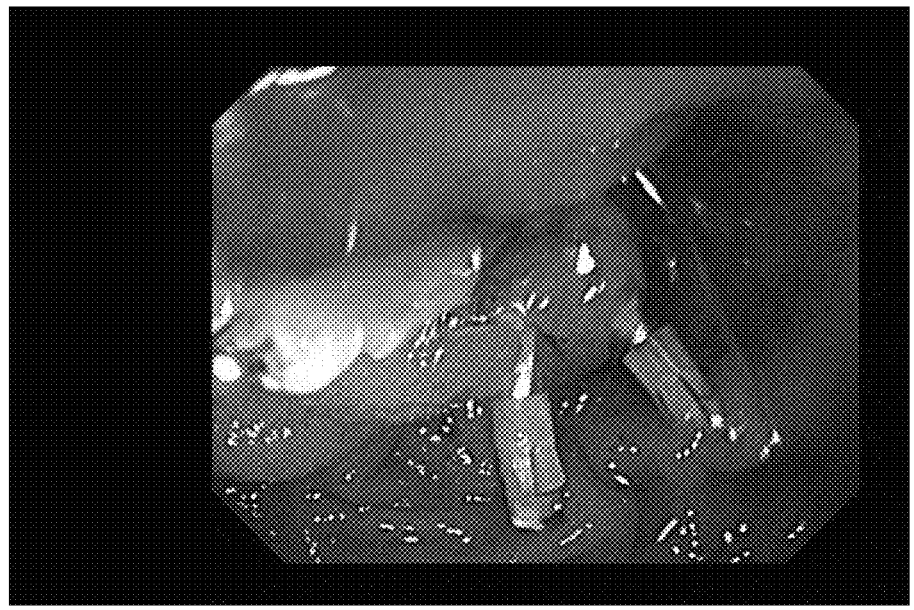
Figure 1F:
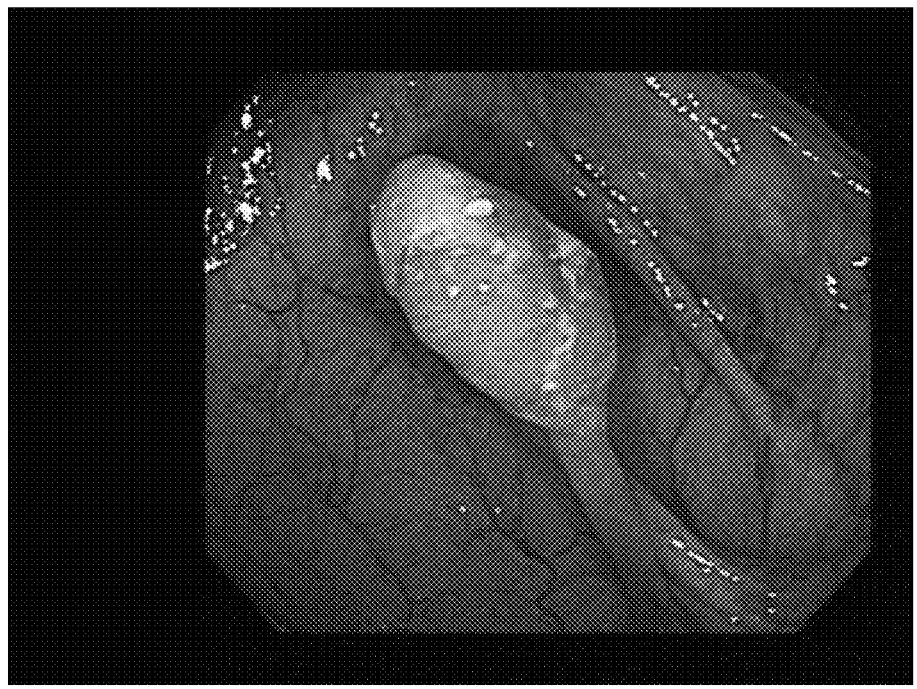
Figure 1G:
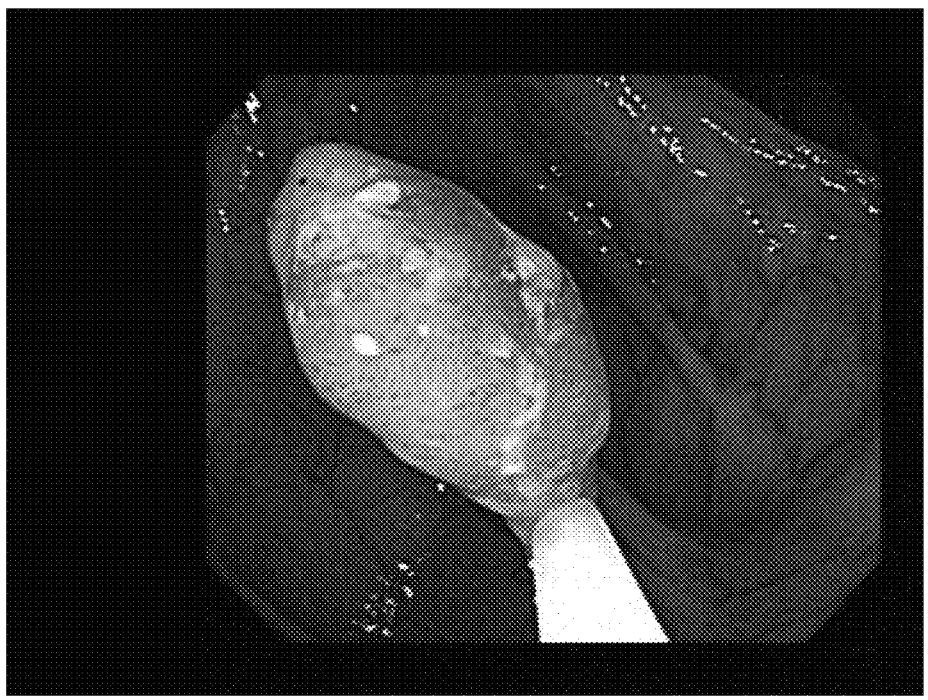
Figure 1H:
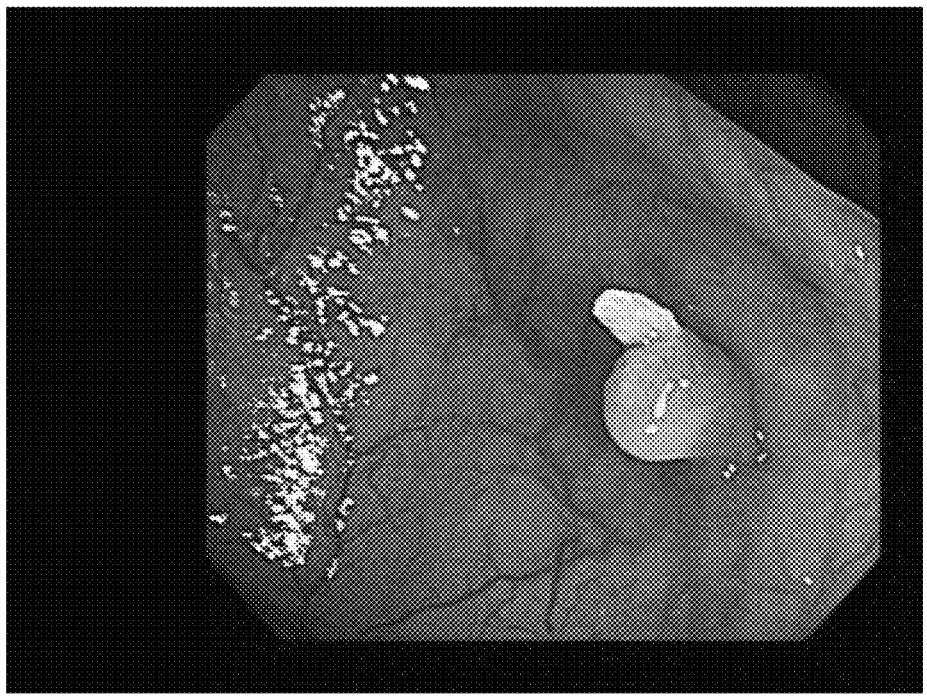
Figure 1I:
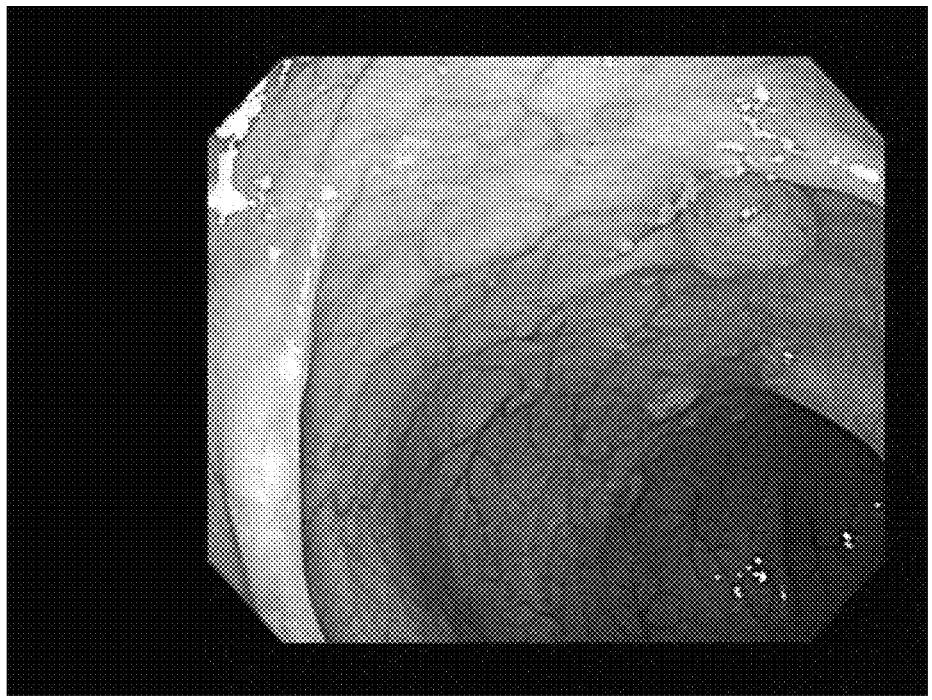
Figure 1J:
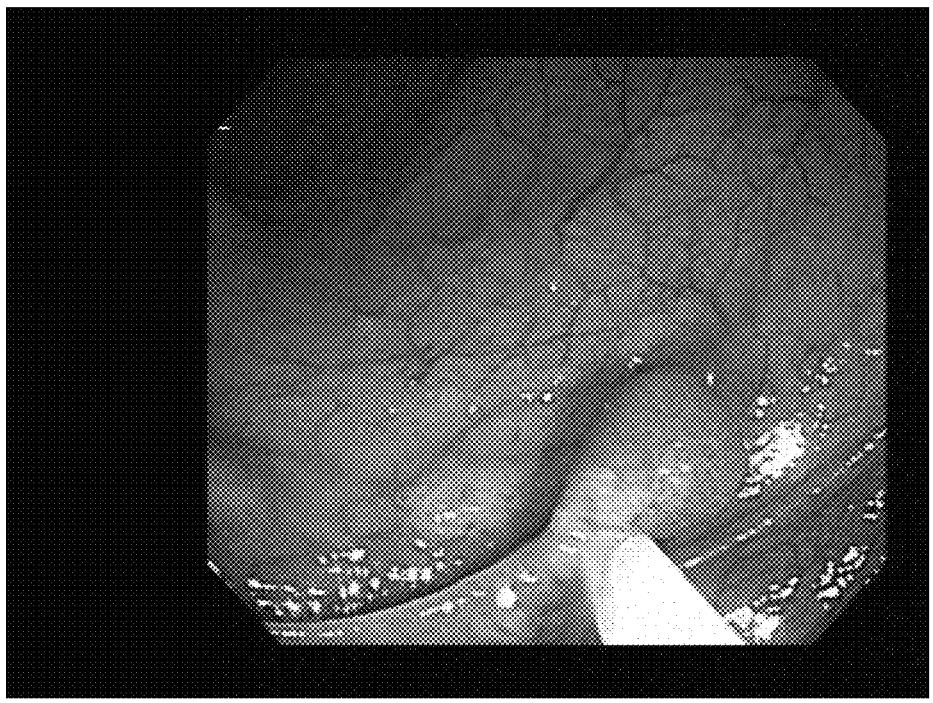
Figure 1K:
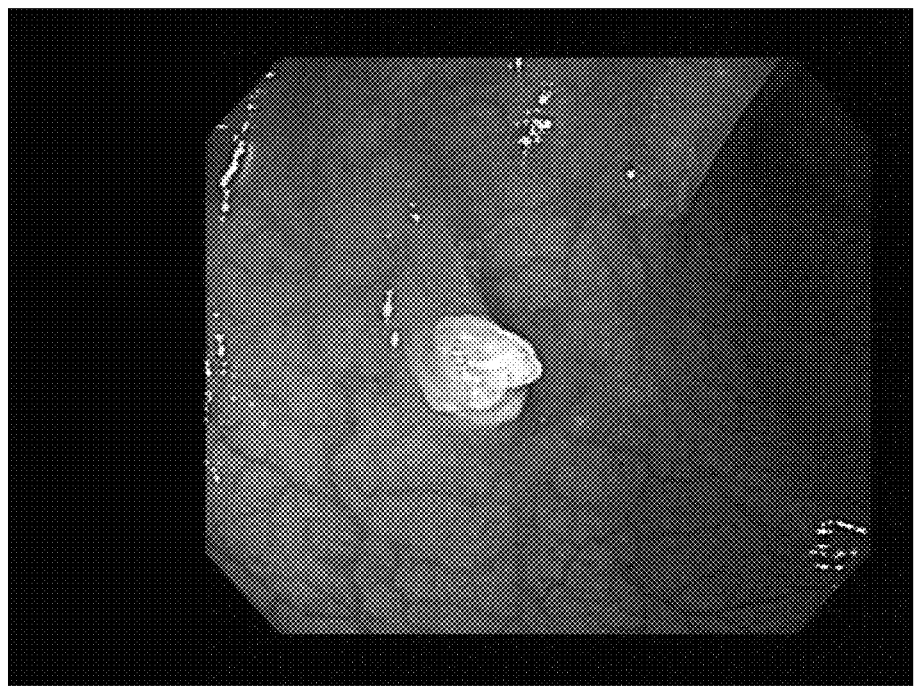
Figure 2A:
Figure 2B:
Figure 2C:
Figure 2D:
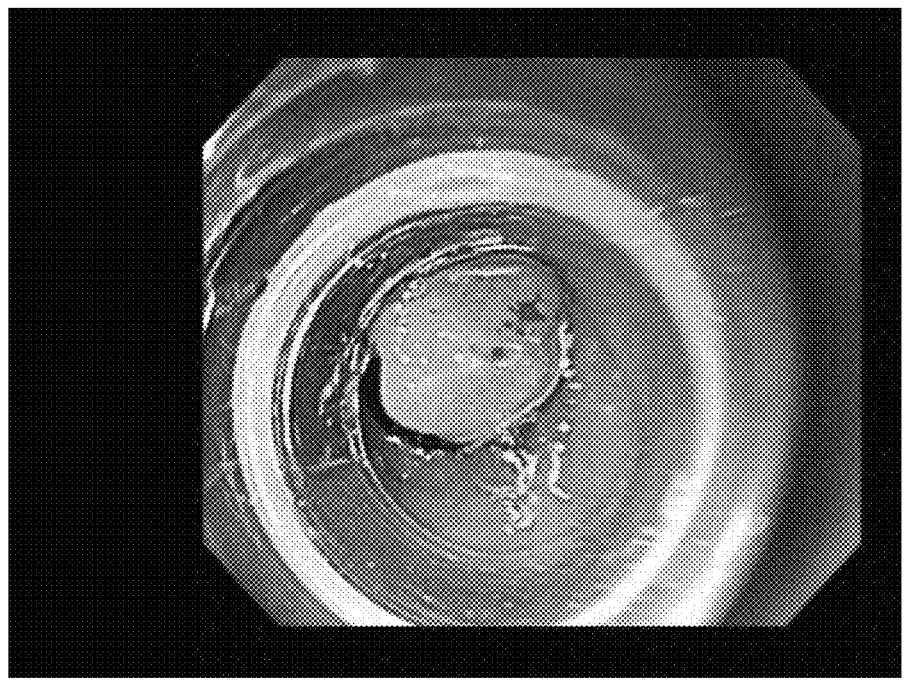
Figure 2E:
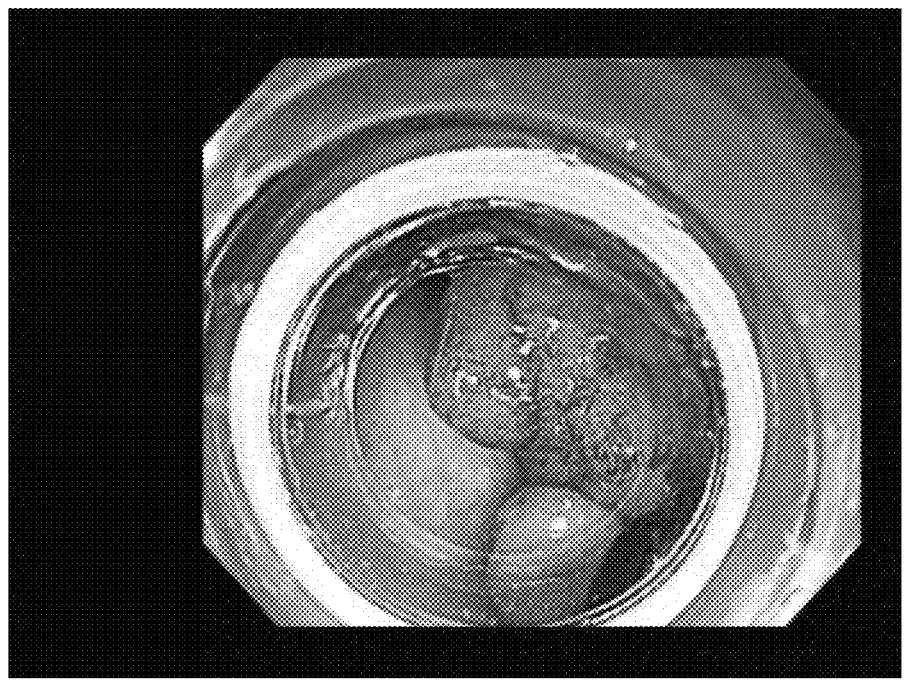
Figure 2F:
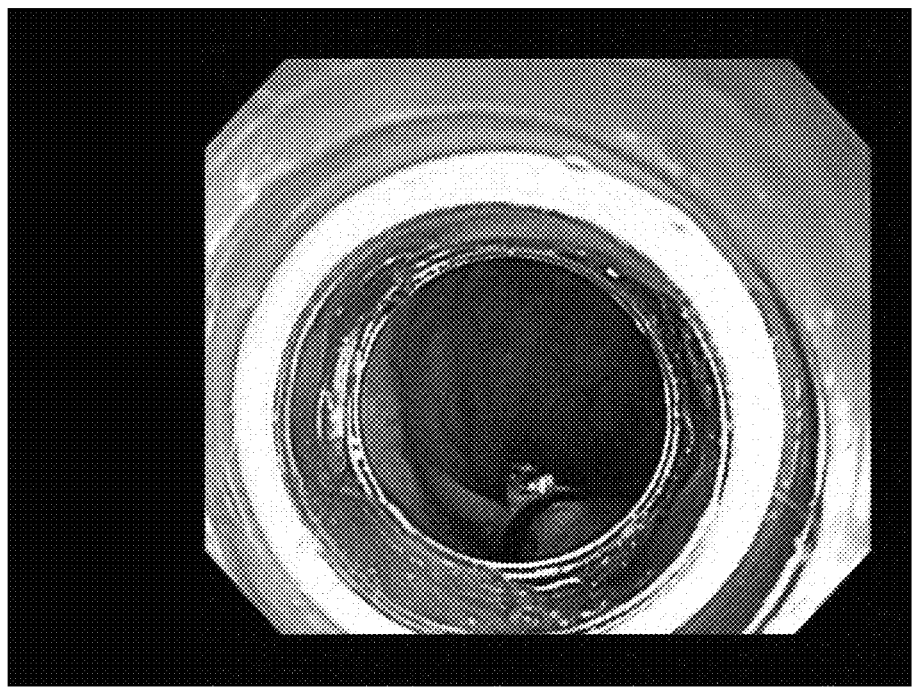
Figure 2G:
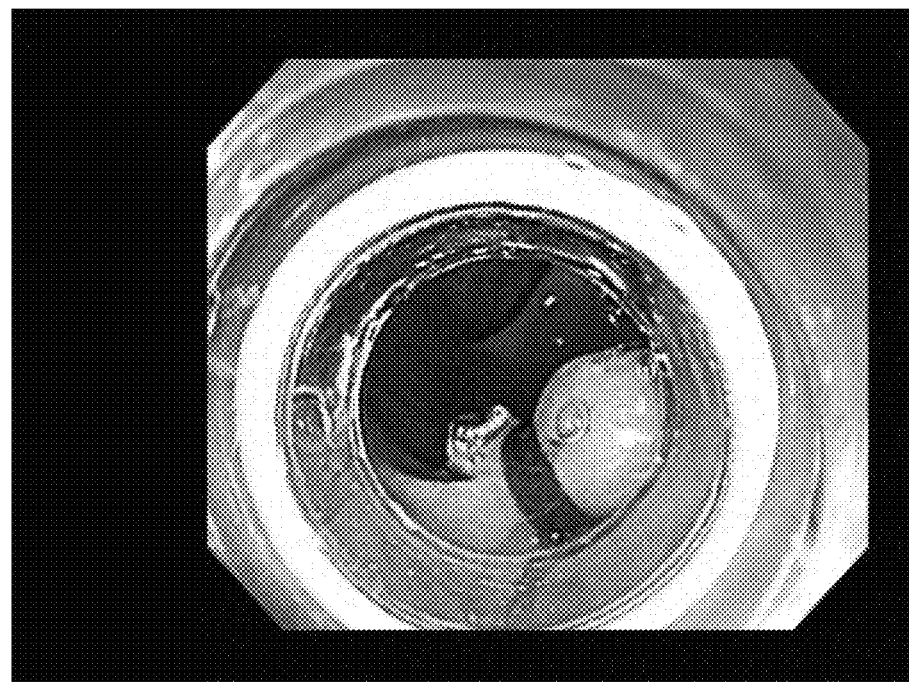
Figures 3A, 3B:
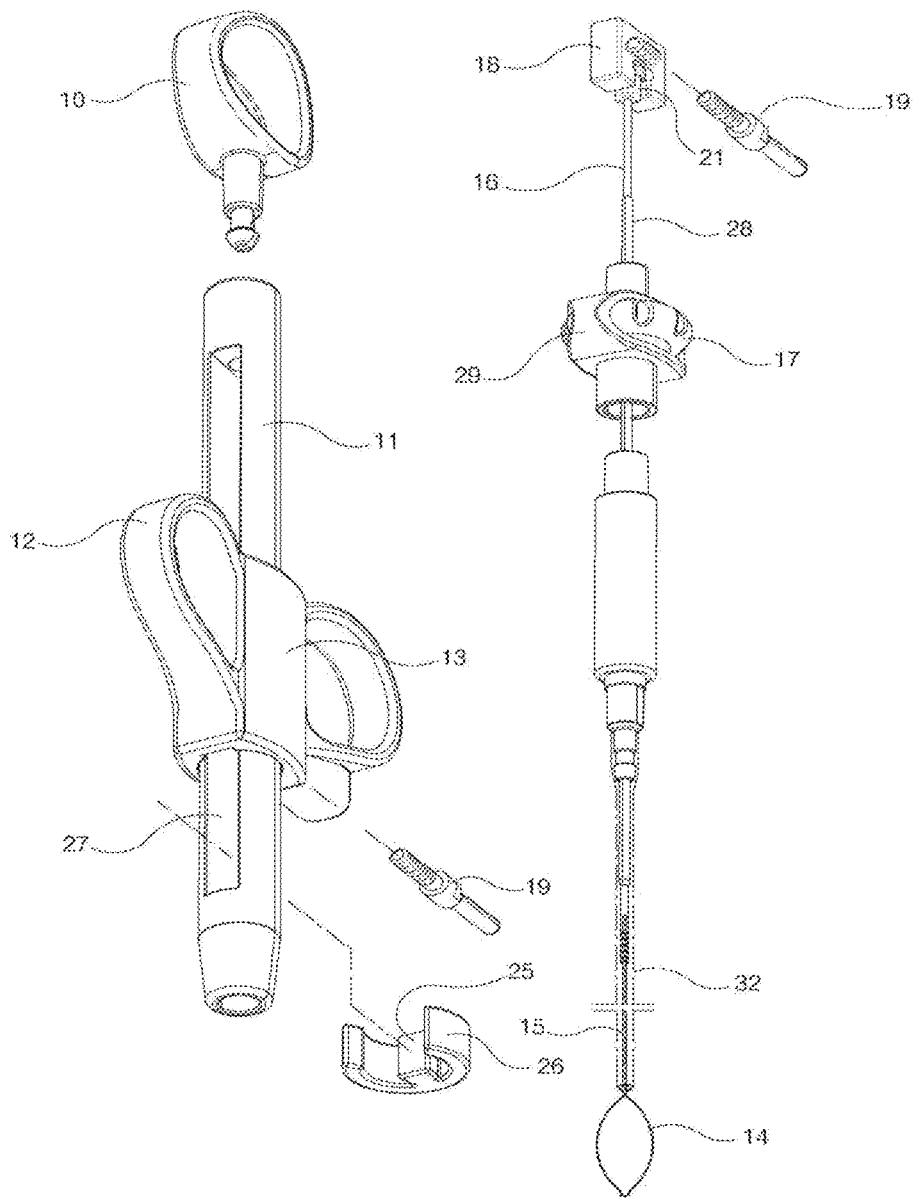
FIGS. 3A to 3E show an example of a medical snare according to the present invention.
Figures 3C, 3D, 3E:
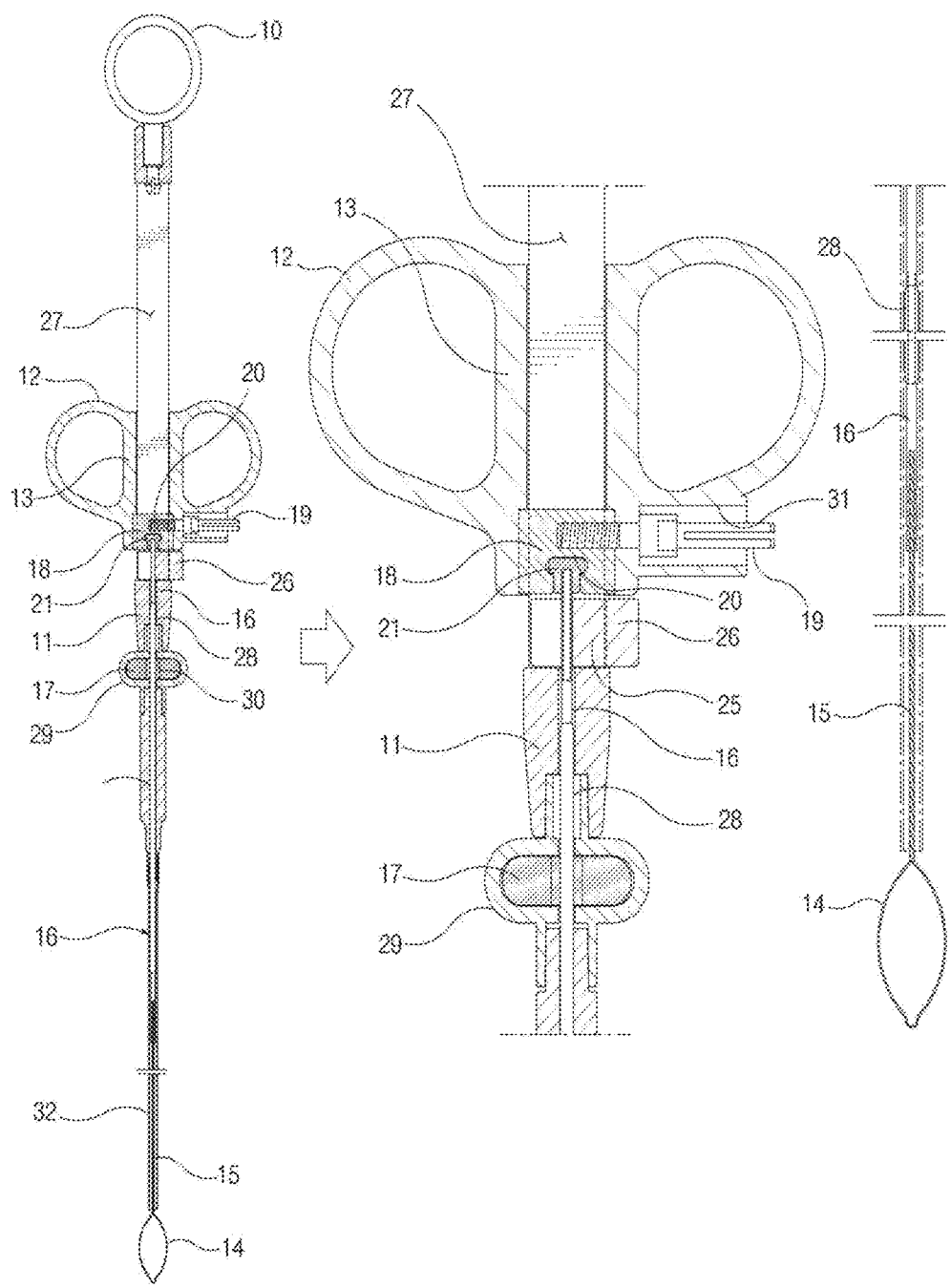

FIGS. 1A and 1B show a specific example of esophageal varix bleeding as a complication of liver cirrhosis according to the present invention.

Referring to FIG. 1A, a bleeding process due to esophageal varix and etc. is shown. Referring to FIG. 1B, a specific method for stopping the bleeding by adhering a rubber ring to a tip end of the endo scope is shown.

This transparent cap may be used not only for stopping the bleeding but also for excising the polyp.

In addition, FIGS. 1C to 1K show a specific example of colonoscopic polypectomy commonly applied according to the present invention.

In general, this polypectomy is widely used in colonoscopy but its usage is not limited to the colon.

In addition, FIGS. 2A to 2G show another example of colonoscopic polypectomy according to the present invention.

Referring to FIGS. 2A to 2G, colonoscopic polypectomy cuts polyps by introducing a punch forceps or a snare made of a special metal through a working channel of an endoscope.

When performing this colonoscopic polypectomy, small polyps are cut with a punch forceps. Meanwhile, big polyps are removed by passing electricity through when the polyp is grasped with a snare so as to prevent bleeding.

In addition, if polyps occurring on the colon mucosa are large and broadly attached, submucosal injection of saline is involved so as to reduce electrical damage to the colon wall before excising the polyps with a snare.

Commonly, a snare used for polypectomy is formed with a tensile rope, wherein the tensile rope ends at the front end portion by being inserted into the snare having a semicircle like shape and the snare has a peak.

The tensile rope is guided to move easily inside a bushing and a corresponding stopper member, wherein the corresponding stopper member has a pipe shape and is disposed at an end portion of the bushing. As one end portion of two snare legs is fixed to the tensile rope, the snare is consequently transferred from a storage position where the snare is placed inside the bushing in a state of being elongated by the tensile rope, to a use position where the snare is placed in the front of an end portion of the bushing.

In addition, an end portion of another snare leg being inside the bushing is connected to a stopper which moves toward the corresponding stopper when taking out the snare from the bushing. Consequently, if the snare leg continues moving, the snare is expanded into a semicircle shape.

However, in the case of a conventional snare for polypectomy, an endoscope is inserted into a part where a polyp that is to be removed occurs, together with a snare. Then, the whole apparatus should be turned so as to turn the snare to the direction in which the polyp occurs. Accordingly, the polyp can be smoothly inserted into the snare. In this case, since the whole apparatus is turned, hardly can an endoscopist turn the snare smoothly to the desired direction and may further have a strained wrist.

In order to solve these problems, a medical snare explained in FIGS. 3A to 3E may be applied.

Figures 4A, 4B, 4C:
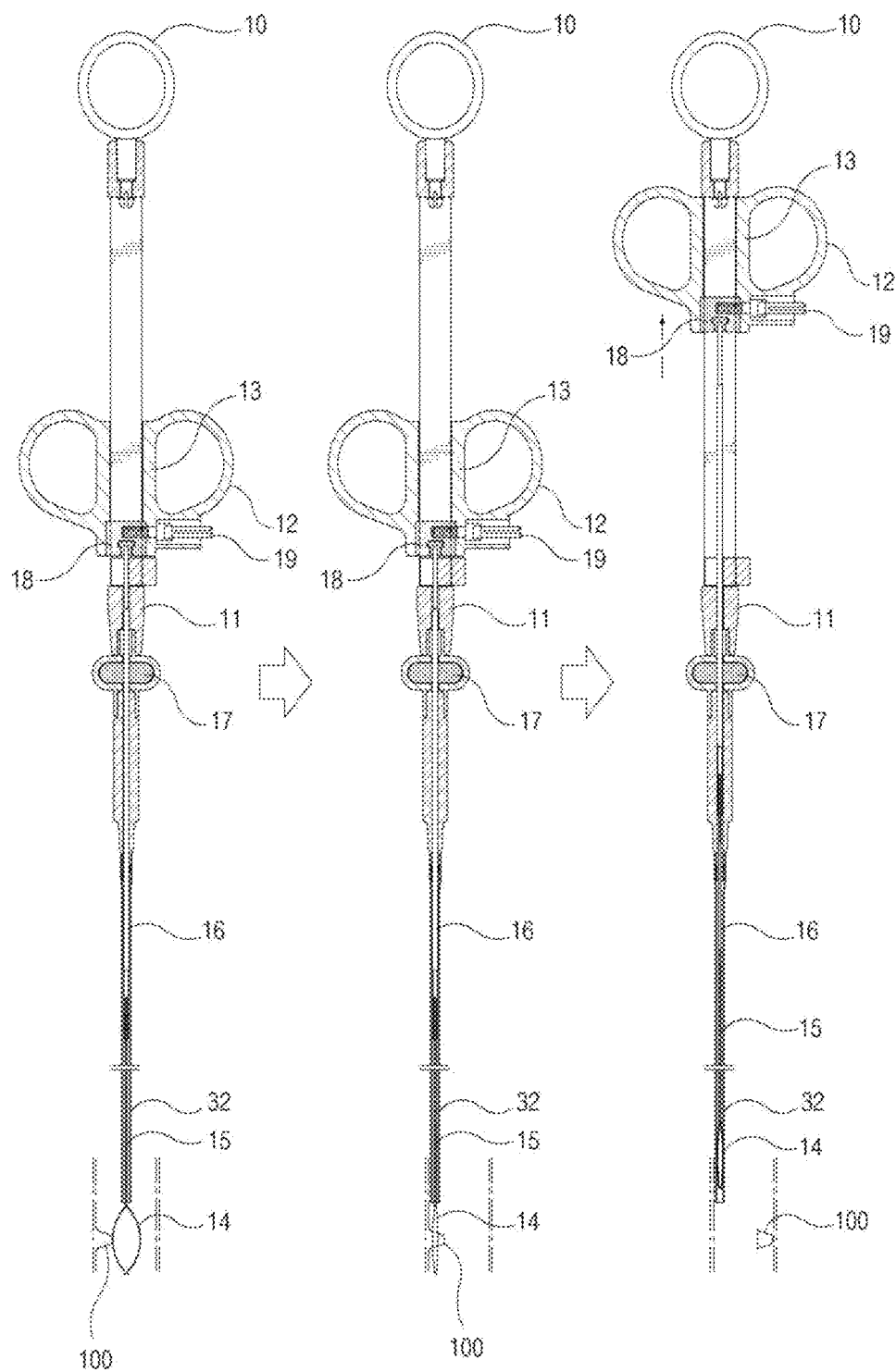
FIGS. 4A to 4C show a view to explain an example of the using state of a medical snare according to the present invention.

That is, FIGS. 3A to 3E show an example of a medical snare according to the present invention, and FIGS. 4A to 4C show a view to explain the using state of a medical snare according to the present invention.

Referring to FIGS. 3A to 3E, a medical snare is capable of controlling the development direction of the snare by turning only a wire through simple manipulation of a knob without turning the whole snare. In particular, it is structured such that the whole wire supporting pipe including the wire is capable of turning around the connection part of a conductive block side as a support point, when manipulating the knob using a turning structure between a wire side and the conductive block side.

For this, the medical snare includes a body 11 corresponding to a main body of the snare. The body 11 has a hollow tubular shape, that is, for example, a pipe shape which has a hole structure formed alongside the central axis and further has a slide hole 27 penetrated and incised to the diameter direction.

At this time, the slide hole 27 is formed over a predetermined section along the length direction of the body 11 and a conductive block 18 of a slider 13 to be described later is positioned thereon, so as to be guided by the slider 13.

A first handle 10 having a ring shape is equipped to an upper end of this body 11 to be in a line, wherein the first handle 10 may be used for the insertion of a thumb when gripping the snare.

Further, the medical snare includes the slider 13 as a means to push or pull a wire.

The slider 13 is inserted around the outer circumference of the body 11 into a concentric circle form, and is then coupled to enable moving along the length direction of the body 11.

Second handles 12 having a ring shape are formed on opposite sides of the slider 13 as a pair, wherein the second handles 12 may be used for the simultaneous insertion of an index finger and a middle finger when gripping the snare.

Further, the snare includes a wire 15 and a wire supporting pipe 16 as a means to substantially cut a polyp when performing polypectomy.

The wire 15 and the wire supporting pipe 16 are coupled to each other linearly, wherein an upper end of the wire 15 is inserted into a lower end of the wire supporting pipe 16, and is then followed by compression to be coupled together in one body.

A snare 14 is formed at a lower end of the wire 15 to grasp and cut a polyp.

The wire supporting pipe 16 is inserted through a hole structure at a lower end of the body 11, and then coupled to a side of a conductive block 18 in the slider 13 through an upper end thereof.

Accordingly, if the slider 13 is moved, the wire supporting pipe 16 and the wire 15 are also moved together along therewith. Consequently, the wire 15 and the wire supporting pipe 16 are capable of cutting a polyp through this motion.

At this time, part of a length of the wire supporting pipe 16 is formed to be a flat plate portion 28 in a shape that a pipe is pressed flat. The flat plate portion 28 may be bound to a knob 17 side to be described later.

Accordingly, when manipulating the knob 17, the whole of the wire supporting pipe 16 and the wire 15 may be turned together to the manipulation direction of the knob 17.

Further, the medical snare includes the knob 17 as a means to turn the wire.

The knob 17 having a rounded dial shape is connected inside a knob housing 29 into a turning structure. Part of the turning structure may be exposed outside the knob housing 29, wherein the knob housing 29 is equipped to the lower end of the body 11 by insertion.

The flat plate portion 28 of the wire supporting pipe 16 may be bound to an axial line of the knob 17 by insertion. Accordingly, if turning the knob 17, the whole of the wire supporting pipe 16 and the wire 15 coupled hereto in one body may be turned.

The interior of the knob 17 is formed with an elastomer 30 to secure a firm binding structure between the knob 17 and the wire supporting pipe 16, wherein as the flat plate portion 28 of the wire supporting pipe 16 is bound inside the elastomer 30 into a compressed structure, the knob 17 and the wire supporting pipe 16 may be thus firmly bounded.

A tube 32 may be equipped to an inner side of a lower end of the knob housing 29 to accommodate the wire 15 and to induce the entry of the wire 15 thereinto.

In addition, the medical snare includes the conductive block 18 and an electrode pin 19, as a means to supply a current to the wire side.

The conductive block 18 having a square shape is equipped to an inner side of a lower end of the slider 13 by insertion.

A rough T-shaped groove portion 20 is formed on a bottom portion of the conductive block 18, wherein an upper end side of the wire supporting pipe 16 may be coupled to the groove portion 20.

Further, the electrode pin 19 is positioned inside a pin insertion hole 31 formed on the side of the slider 13 and is then equipped into a structure to be connected to a side portion of the conductive block 19 through a screw portion of the tip end region.

The electrode pin 19 is coupled to an outside power supply through a conductive wire (not illustrated), then supplied with a current so as to apply the supplied current to the side of the conductive block 18. Consequently, the wire supporting pipe 16 coupled to the side of the conductive block 18 and the continued wire 15 may be in a conducting state.

Especially, the wire supporting pipe 16 is coupled to the side of the conductive block 18 into a turning structure.

For this, a pipe shaped busing 21 which has a rough T-shaped cross section is coupled to the upper end of the wire supporting pipe 16 in one body. As the bushing is coupled to the groove portion 20 of the conductive block 18 into a matching form by insertion, the wire supporting pipe 16 is capable of turning around a self-axial line using, as a support point, a coupling part of the side of the conductive block 18 through the mediation of the bushing 21. Consequently, the whole wire 15 may turn.

Further, the bushing 21 of the wire supporting pipe 16 is hardly detached downwardly inside the groove portion 20 of the conductive block 18 through a T-shaped latch structure.

In addition, the medical snare includes a stopper 26 as a means to control the movement of the whole of the wire 15 and the wire supporting pipe 16.

The stopper 26 has an open ring shape, and is coaxially mounted on an outer circumferential surface of the body 11, so as to enable linear movement along the length direction of the body 11.

Herein, it is preferable that the stopper 26 have an arc length that is larger than the semicircle, so as not to fall out to the radius direction of the body.

Further, a contact protrusion portion 25 is formed on the inner circumferential surface of the stopper 26, wherein the contact protrusion portion 25 is positioned inside the slide hole 27 of the body 11, and thus contacts the wire supporting pipe 16 through a tip end surface thereof.

Accordingly, when moving or turning the wire supporting pipe 16, the position (direction) may be maintained without turning under the contact regulation by the contact protrusion portion 25 of the stopper 26. Consequently, the initial entry direction of the snare, or the direction thereof returning after removing a polyp may be maintained stably.

Especially, the wire supporting pipe contacting the contact protrusion portion 25 has the outer circumference composed of the flat plate portion 28 having a rectangular shape, and is thus provided with a turning supporting force according to every angle of 90 degrees when turning. Referring to FIGS. 4A to 4C, in order to use the snare in surgery, the slider 13 is pulled to the rear maximally, so that the snare 14 can be inserted into the tube 32 when being pressurized.

Under this state, the tube 32 is inserted into the colon together with an endoscope (not illustrated) through the anus.

After then, if the position of polyp 100 is identified by the endoscope, a thumb is inserted into the first handle 10 of the body 11 and an index finger and a middle finger are inserted into the second handle 12 of the slider 13 to grip the snare.

Then, a hand gripping the snare is opened widely to separate the body 11 and the slider 13, so that the snare 14 can be exposed from the tube 32 while expanding.

Like the above, if the snare 14 is exposed from the tube 32, in a state of positioning the polyp 100 inside the spread space of the snare 14, the opened hand gripping the snare is closed, so that the body 11 and the slider 13 may contact each other.

Accordingly, the snare 14 is inserted into the tube 34 with being pressurized and the polyp 100 is then removed by cutting with pressurizing.

Naturally, if a polyp to be removed is large, the polyp may be cut in a state of applying a current.

Meanwhile, if the position where the polyp 100 occurs does not correspond to the spread space of the snare 14, in a state that one hand grips the snare, a knob 17 is turned in the right and left directions by using another hand, so as to turn the wire supporting pipe 16, the wire 15, and the snare 14 together.

Hereby, the direction of the spread space of the snare of the wire 15 is turned to the direction for easy insertion of the polyps 100 occurring in various directions by simply turning the knob 17. Consequently, the polyps 100 may be easily inserted into the spread space of the snare 14.

However, even though using the aforementioned apparatus and method, since the stalk of a polyp is present in a loosely twisted shape, a conventional snare for polypectomy has a problem in that it is difficult to control the portion of the polyp to be sucked between the head and stalk of the polyp and what position is to be cut therebetween. It is moreover difficult to perform surgery.

In addition, since a conventionally used ring is mounted on the outer circumference of the snare and then discharged, time interval occurs when sucking a polyp and fixing it with the ring. There is, thus, a problem in that it is difficult for a user to fix a desired portion of a polyp through the ring.

Therefore, the present invention relates to a medical two-chamber snare (transparent cap) used when performing polypectomy, wherein a snare made of a special metal is introduced through a working channel of an endoscope, and then electricity is passed through when grasping a polyp so as to cut it.

In addition, a folded stalk is spread through a first chamber of the two-chamber snare. The stalk is captured with a ring of a second chamber and a ring is discharged to cramp the stalk including a feeding artery. The head of the polyp is then completely removed. Thus, surgery may be easily performed.

Further, differently from the conventional ring, a ring is equipped to only the second chamber in the two-chamber snare. As the polyp is pulled inside the second chamber, then fixed through a fixer, the initial entry direction of the ring may be maintained stably. It is advantageous in an aspect of the structure. Moreover, it may save time and simplify surgery.

Figure 5A:
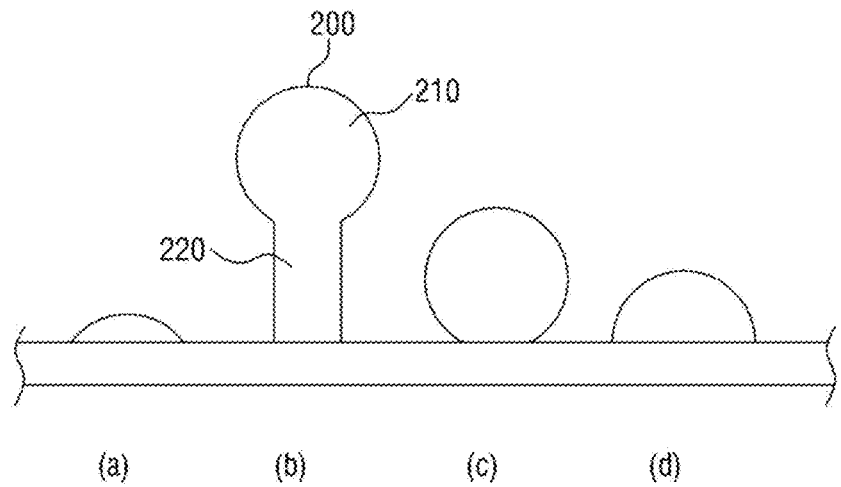
FIGS. 5A to 5C show a view to explain the structure of a snare for removing a tumor according to the present invention.
Figure 5B:
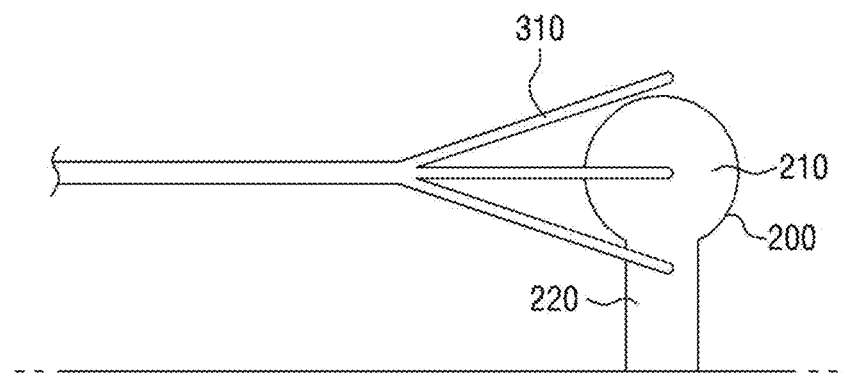
Figure 5C:
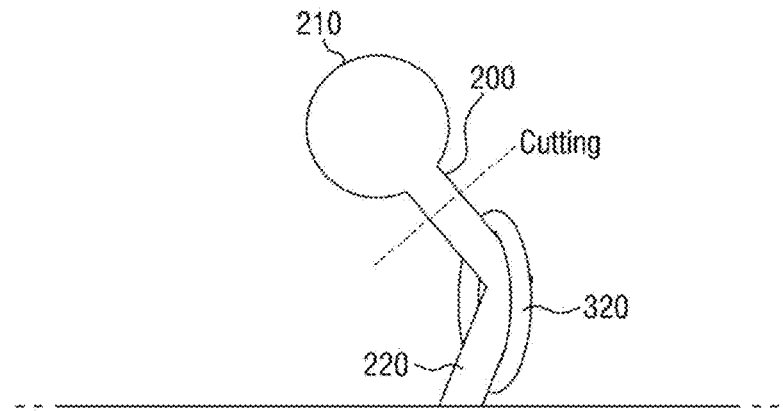

FIGS. 5A to 5C show a view to explain the structure of a snare for removing a tumor according to an embodiment of the present invention.

The tumor is a cell aggregation showing autonomous overgrowth and occurs in cells constituting the living body differently from the parasite.

Referring to FIG. 5A, various types of tumors (a) to (d) are illustrated.

Like the tumor (b) among tumors (a) to (d) as shown in FIG. 5A, there may be a tumor 200 including a head 210 and a stalk 220, that is, a polyp.

A typical polyp is a colon polyp occurring in the colon. However, polyps may occur in other organs of the living body and these polyps 200 have a stalk besides a head.

In the polyp 200, the head 210 is a dangerous portion to the human body. Thus, a portion including the head 210 should be completely excised, so as to prevent diseases possibly occurring later.

A method using an apparatus having a tripod structure 310 may be used as a method for removing a polyp having a stalk, based on the configuration of the aforementioned snare.

Referring to FIG. 5B, the stalk 220 is sucked with the head 210 through the tripod structure 310. As shown in FIG. 5C, the polyp 200 is then fixed through a ring 320 to perform excision.

However, since the stalk of a polyp is not present in practice in a linear type but in a loosely twisted type, the method using the tripod structure 310 may suck and fix only the stalk 220 without the head 210 or may fix and remove a part of the head 210.

That is, failing to completely remove the head 210, hardly could a tissue excision be performed perfectly, and there is a problem in that this may induce diseases possibly occurring later.

Therefore, the present invention relates to a medical two-chamber snare (transparent cap) used when performing polypectomy, wherein a snare made of a special metal is introduced through a working channel of an endoscope, and then electricity is passed through when grasping a polyp so as to cut it.

In particular, the present invention relates to a two-chamber snare which spreads a stalk folded loosely through a first chamber, fixes a polyp with a ring through a second chamber, and then clearly removes a head of the polyp, so as to make surgery easier.

Referring to FIGS. 6A to 6C, a transparent cap 400 for removing a tumor according to the present invention is explained particularly.

FIGS. 6A to 6C show a view to explain the structure of a two-chamber snare for removing a tumor according to the present invention.

Referring to FIG. 6C, the snare (transparent cap) 400 for removing a tumor according to the present invention basically has a structure that is partitioned into a first chamber 410 and a second chamber 420.

In addition, the ring 320 may be mounted on the outer circumference of the snare 400 to fix a polyp.

The first chamber 410 and the second chamber 420 are equipped with a first tube 430 and a second tube 440 respectively.

In addition, a snare 460 having a hook as shown in FIG. 6A or a snare 450 having a tripod as shown in FIG. 6B may be equipped to the end of a first tube 430.

Similarly, a snare 460 having a hook as shown in FIG. 6A or a snare 450 having a tripod as shown in FIG. 6B may be equipped to the end of a second tube 440.

As the snare 450 of the first tube 430 and the snare 460 of the second tube 440 are illustrated by example in FIGS. 6A and 6B, respectively, the present invention is not limited thereto and it is obvious that the snares 450, 460 may be implemented in various forms to fix an object.

Consequently, as the snare 460 of the second tube 440 hooks the stalk 220, provided is a function to untwist the twisted stalk 220.

In addition, the snare 450 of the first tube 430 fixes the stalk 220 of a region entirely including the head 210 on the basis of the untwisted stalk 220 with the ring 320.

Then, removing the stalk 220 of the region entirely including the head 210 portion fixed through the ring 320, the existing problems may be completely resolved.

Detailed operations of the present invention will be described using FIG. 7 on the basis of the aforementioned contents of FIGS. 6A to 6C.

Figure 7:
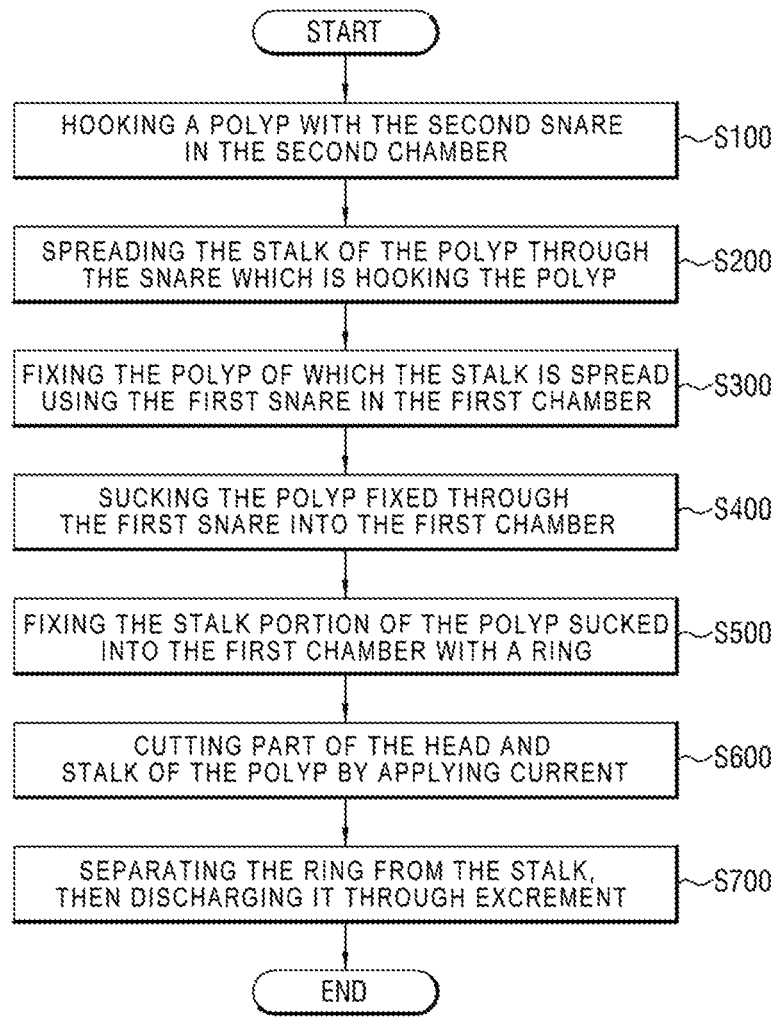
FIG. 7 shows a flowchart to explain a method for excising a polyp using the two-chamber snare explained in FIGS. 6A to 6C.

FIG. 7 shows a flowchart to explain a method for excising a polyp using the two-chamber snare explained in FIG. 6A to 6C.

Referring to FIG. 7, the second snare 460 in the second chamber 420 hooks the polyp 200 at step S100.

Then, the stalk 220 of the polyp is spread through the snare 460 which is hooking the polyp 200 at step S200.

In addition, the polyp 200 of which the stalk 220 is spread is fixed using the first snare 450 in the first chamber 410 at step S300.

That is, the first snare 450 implemented as the tripod or hook type fixes an upper portion of the stalk 220 which entirely includes the head 210 in the spread polyp, before discharging the ring 320.

Then, the polyp 200 fixed through the first snare 450 is sucked into the first chamber 410 at step S400.

In addition, the stalk 220 of the polyp sucked into the first chamber 410, that is, a lower portion of the stalk 220 entirely including the head 210 is fixed with the ring at step S500.

Then, part of the head 210 and the stalk 220 of the polyp 200 is cut by applying a current at step S600. The ring is separated from the stalk, and then discharged through excrement at step S700.

FIGS. 8A to 8D show a view to explain particular steps of the method shown in FIG. 7.

Figure 8A:
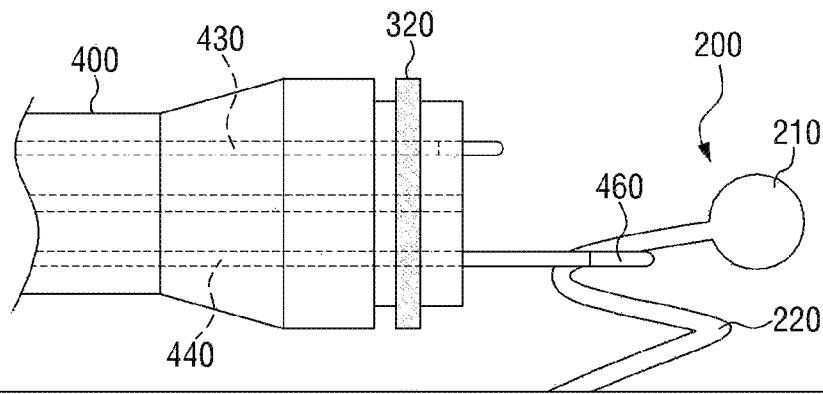
FIGS. 8A to 8D show a view to explain particular steps of the method shown in FIG. 7.

FIG. 8A shows step S100 in FIG. 7.

Referring to FIG. 8A, the second snare 460 in the second chamber 420 hooks the polyp 200.

Figure 8B:
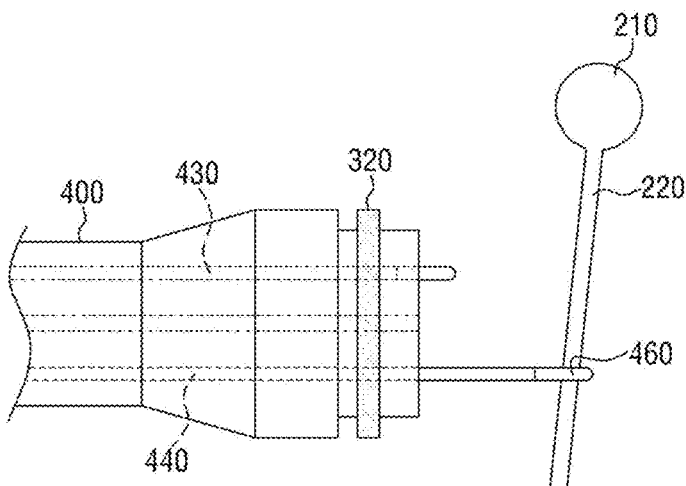

Further, FIG. 8B shows step S200 in FIG. 7.

Referring to FIG. 8B, the stalk 220 of the polyp is spread through the snare 460 which is hooking the polyp 200.

Figure 8C:
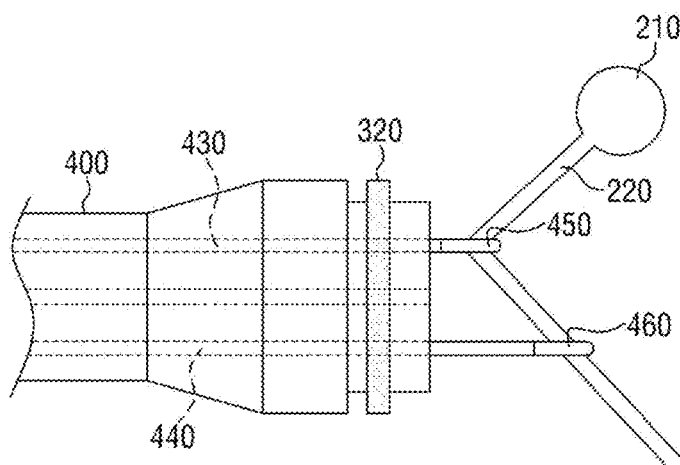

Further, FIG. 8C shows step S300 in FIG. 7.

Referring to FIG. 8C, the polyp 200 of which the stalk 200 is spread is fixed using the first snare 450 in the first chamber 410.

Figure 8D:
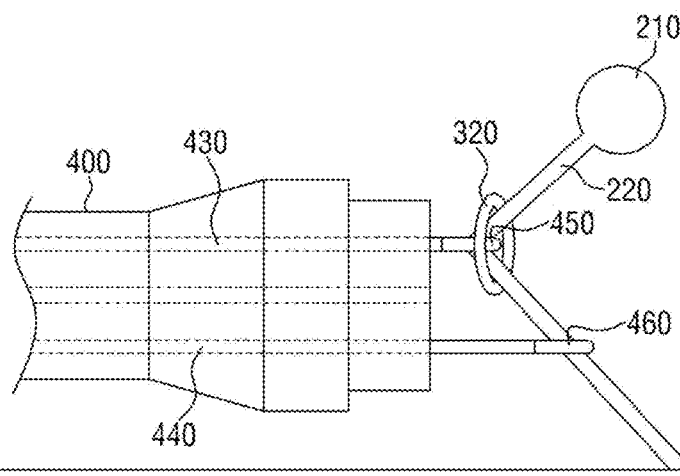

Further, FIG. 8D shows steps S400 and S500 in FIG. 7.

Referring to FIG. 8D, the polyp 200 fixed through the first snare 450 is sucked into the first chamber 410. The stalk 220 of the polyp sucked into the first chamber 410, that is, the lower portion of the stalk 220 entirely including the head 210 is fixed with the ring 320.

Therefore, according to the configuration of the present invention, the bent polyp is straightened through the second chamber in the two-chamber snare. The polyp is then fixed with the ring through the first chamber to completely remove the head of the polyp thereby making surgery easier.

In addition, differently from the conventional ring, a ring is equipped to only the first chamber in the two-chamber snare. As the polyp is pulled inside the first chamber, then fixed through a fixer, the initial entry direction of the ring may be maintained stably. It is advantageous in an aspect of the structure. Moreover, it may save time and simplify surgery.

Meanwhile, for convenience, the present invention supposes that the number of chambers in the snare (transparent cap) 400 is two (2), however, it is not limited thereto.

That is, as the snare (transparent cap) 400 is constituted of two or more chambers, it may be possible to implement the snare (transparent cap) 400 capable of providing various additional functions.

Meanwhile, as the aforementioned ring 320 is mounted on the outer circumference of the snare 400, then discharged, time interval occurs when sucking the polyp 200 and fixing it with the ring 320. There is, thus, a drawback in that it is difficult for a user to fix a desired portion of the polyp 200 through the ring.

Therefore, according to the present invention, differently from the conventional ring, a ring is equipped to only the first chamber in the two-chamber snare. As the polyp is pulled inside the first chamber, then fixed through a fixer, the initial entry direction of the ring may be maintained stably. It is advantageous in an aspect of the structure. Moreover, it may save time and simplify surgery.

Figure 9A:
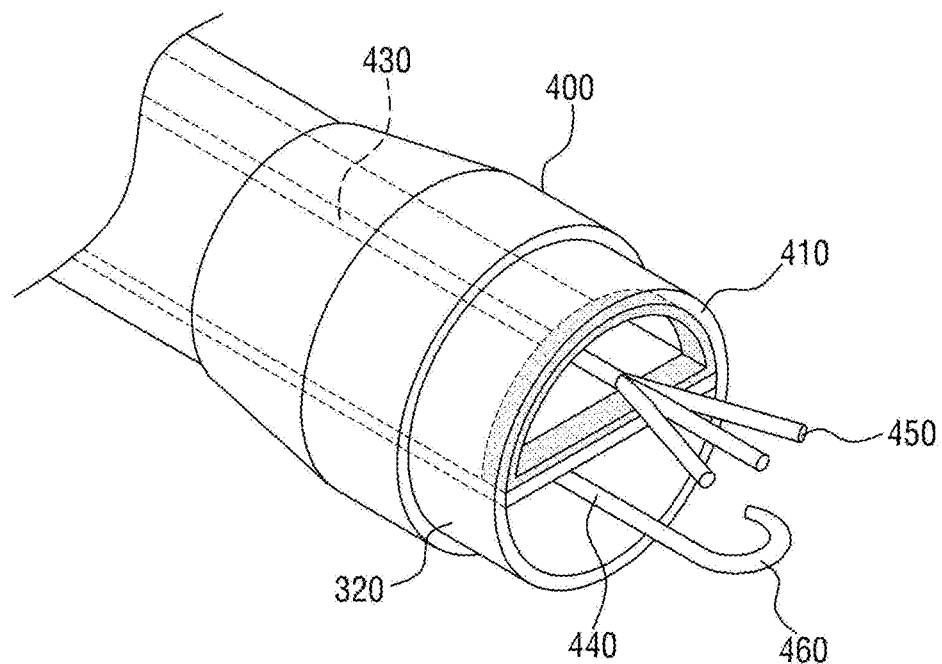
FIGS. 9A and 9B show another view to explain the structure of a two-chamber snare for removing a tumor according to the present invention.
Figure 9B:
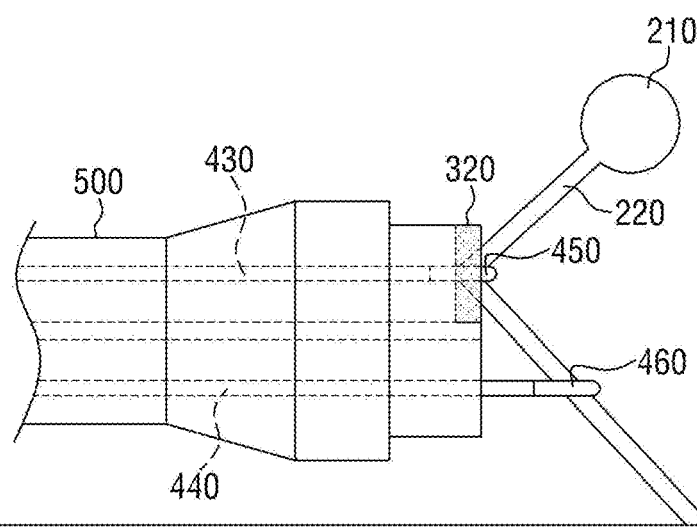

FIGS. 9A and 9B show a view to explain the structure of a two-chamber snare for removing a tumor according to another example embodiment of the present invention.

Referring to FIG. 9A, the structure of the newly supposed example embodiment of snare 400 is basically the same as the one explained in FIGS. 6A to 6C.

The ring 320 is merely present inside the outer circumference of the first chamber 410 in FIG. 9A.

That is, the ring 320 is present on the entire outer circumference of the snare 400 in FIG. 6C. On the contrary, the ring 320 is present inside the outer circumference of the first chamber 410 in FIG. 9A.

Therefore, the structure according to the exemplary embodiment of the present invention is greatly effective in carrying out steps S400 and S500, wherein the polyp 200 fixed through the first snare 450 is sucked into the first chamber 410 at step S400, and the stalk 220 of the polyp sucked into the first chamber 410, that is, a lower portion of the stalk 220 entirely including the head 210 is fixed with a ring at step S500.

That is, when the polyp 200 is sucked into the first chamber 410, the concerned polyp 200 is fixed not with the ring 320 of the entire outer circumference of the snare 400, but with the ring 320 directly discharged from inside the outer circumference of the first chamber 410. Thus, it enables a user to fix the desired lower portion of the stalk 220 precisely.

Therefore, according to the aforementioned configuration of the present invention, provided is a medical two-chamber snare used when performing polypectomy, wherein a snare made of a special metal is introduced through a working channel of an endoscope, then electricity is passed through when grasping a polyp so as to cut it.

In addition, the bent polyp is straightened through the first chamber in the two-chamber snare. The polyp is then fixed with the ring through the second chamber to completely remove the head of the polyp thereby making surgery easier.

Further, differently from the conventional ring, a ring is equipped to only the first chamber in the two-chamber snare. As the polyp is pulled inside the first chamber, then fixed through a fixer, the initial entry direction of the ring may be maintained stably. It is advantageous in an aspect of the structure. Moreover, it may save time and simplify surgery.

Meanwhile, for convenience, the present invention supposes that the number of the ring 320 is one (1), however, it is not limited thereto.

That is, as a plurality of rings 320 are used at the same time, and then discharged to the outside one by one, they may be used in removing heads of a plurality of polyps.

As described above, the detailed description for the disclosed preferable embodiments of the present invention is provided to those skilled in the art so as to conceive and implement the present invention. In the above, the present invention was described by referring to preferable example embodiments. However, it will be understood that those skilled in the art may modify and alter the present invention diversely within the scope of the present invention. For example, those skilled in the art may use the respective configurations of the present invention which are explained in detail in the above described example embodiments by a combination thereof. Therefore, the present invention is not limited to the embodiment forms described herein but it is intended to provide the widest scope corresponding to the principles and novel features disclosed herein.

The present invention may be reified into other special forms within the concepts and essential features of the present invention. Therefore, the above detailed description is not limitative to every aspect but will be considered as illustrations by example. The scope of the present invention will be determined by reasonable interpretation of claimed invention attached herewith and every modification within the equivalent scope of the present invention will be included in the scope of the present invention. The present invention is not limited to the embodiment forms described herein but it is intended to provide the widest scope corresponding to the principles and novel features disclosed herein. In addition, claims which have no explicit citation relationship in the scope of the claimed invention may be combined with each other to configure embodiments or may be included as new claims through an amendment after filing application.

What is claimed is:

1. A snare system to remove a polyp, the snare system comprising:
    an endoscope comprising a first working channel, a second working channel, and a snare transparent cap, the snare transparent cap having a body of a hollow tubular shape with an interior partitioned into a plurality of chambers, the plurality of chambers comprising at least a first chamber and a second chamber, the first chamber associated with the first working channel, and the second chamber associated with the second working channel;
    a first snare and a second snare, wherein the second snare is configured to be discharged through the second working channel and outside the second chamber to hook and spread a stalk of the polyp, wherein the first snare is configured to be discharged through the first working channel and outside the first chamber to hook a first portion of the stalk as spread by the second snare and to pull the first portion into the first chamber, the first portion including a head of the polyp, and wherein the second snare and the first snare are at least one of a hook type snare and a multi-legged type snare; and
    a ring mounted on an outer circumference of the first chamber using elasticity, the ring configured to be discharged via the endoscope from the outer circumference and through the elasticity shrink to fix the first portion as hooked by the first snare, wherein the head of the polyp is removable by excision of an upper portion of the first portion using a current of the first snare, the upper portion including the head of the polyp.

* * * * *